(12) United States Patent
Piantoni et al.

(10) Patent No.: US 11,191,674 B2
(45) Date of Patent: Dec. 7, 2021

(54) APPARATUS AND METHOD FOR FORMING AN ABSORBENT PAD

(71) Applicant: GDM S.p.A., Bologna (IT)

(72) Inventors: Matteo Piantoni, Albino (IT); Valerio Soli, Bologna (IT); Marco Rosani, Vailarate (IT); Federico Toscani, Castelleone (IT); Giuseppe Poli, Cumignano sul Naviglio (IT)

(73) Assignee: GDM S.P.A., Bologna (IT)

( * ) Notice: Subject to any disclaimer, the term of this patent is extended or adjusted under 35 U.S.C. 154(b) by 132 days.

(21) Appl. No.: 16/492,018

(22) PCT Filed: Jan. 26, 2018

(86) PCT No.: PCT/IB2018/050475
§ 371 (c)(1),
(2) Date: Sep. 6, 2019

(87) PCT Pub. No.: WO2018/172860
PCT Pub. Date: Sep. 27, 2018

(65) Prior Publication Data
US 2020/0345558 A1    Nov. 5, 2020

(30) Foreign Application Priority Data

Mar. 22, 2017 (IT) .......................... 102017000031317

(51) Int. Cl.
*A61F 13/15*    (2006.01)
*A61F 13/47*    (2006.01)
(Continued)

(52) U.S. Cl.
CPC .. *A61F 13/15658* (2013.01); *A61F 13/15634* (2013.01); *A61F 13/15699* (2013.01);
(Continued)

(58) Field of Classification Search
CPC .......... A61F 13/15634; A61F 13/15658; A61F 13/15699; A61F 13/15804; A61F 13/4704;
(Continued)

(56) References Cited

U.S. PATENT DOCUMENTS 4,216,687 A      8/1980  Dickover et al.
6,573,422 B1 *   6/2003  Rosenfeld ........... A61F 13/4756
                                              604/368
(Continued)

FOREIGN PATENT DOCUMENTS

CN      105960224      9/2016
EP      0226939 A2     7/1987
(Continued)

OTHER PUBLICATIONS

Machine translation of the foreign priority document, IT102017000119095, for US Patent Application Publication US 2019/0142649 to Sablone et al. The priority document was filed Oct. 20, 2017, but the date of publication is unknown. (Year: 2017).*

(Continued)

*Primary Examiner* — Michael A Tolin
(74) *Attorney, Agent, or Firm* — Shuttleworth & Ingersoll, PLC; Timothy Klima (57) ABSTRACT

A method for forming an absorbent pad including a first layer, a second layer and an absorbent material interposed between the first and the second layer and arranged according to a spreading pattern M1 having at least one channel which is free of absorbent material, includes a step of feeding a first web, intended to form the first layer of the pad; a step of feeding a second web, intended to form the second layer of the pad; a step of spreading the absorbent material on the first web according to the spreading pattern M1; a step of joining the first and second webs, a step of (Continued)

removing any absorbent material that may be present in the channel.

20 Claims, 3 Drawing Sheets (51) Int. Cl.
    *A61F 13/53*     (2006.01)
    *B32B 5/26*     (2006.01)
    *B32B 5/02*     (2006.01)
    *B32B 7/14*     (2006.01)

(52) U.S. Cl.
    CPC .... *A61F 13/15804* (2013.01); *A61F 13/4704* (2013.01); *B32B 5/022* (2013.01); *B32B 5/26* (2013.01); *B32B 7/14* (2013.01); *A61F 2013/1591* (2013.01); *A61F 2013/530481* (2013.01); *A61F 2013/530868* (2013.01); *B32B 2262/062* (2013.01); *B32B 2307/726* (2013.01); *B32B 2535/00* (2013.01)

(58) Field of Classification Search
    CPC .............. A61F 13/49001; A61F 13/532; A61F 13/5323; A61F 2013/15869; A61F 2013/1591; A61F 2013/15926; A61F 2013/530007; A61F 2013/530481; A61F 2013/530489; A61F 2013/530591; A61F 2013/530868; A61F 2013/53908; B32B 5/022; B32B 5/26; B32B 7/14; B32B 2262/062; B32B 2307/726; B32B 2535/00
See application file for complete search history.

(56) References Cited

U.S. PATENT DOCUMENTS

| | | | |
|---|---|---|---|
| 8,057,620 | B2 | 11/2011 | Perego et al. |
| 8,604,270 | B2 | 12/2013 | Venturino et al. |
| 2007/0039690 | A1* | 2/2007 | Walsh ............... A61F 13/15658 156/290 |
| 2011/0042844 | A1 | 2/2011 | Brown et al. |
| 2012/0059342 | A1 | 3/2012 | Kinoshita et al. |
| 2014/0039437 | A1* | 2/2014 | Van De Maele ... A61F 13/5323 604/384 |
| 2014/0296817 | A1* | 10/2014 | Malderen ................. D04H 1/70 604/385.01 |
| 2014/0371701 | A1* | 12/2014 | Bianchi ............. A61F 13/53743 604/378 |
| 2019/0142649 | A1* | 5/2019 | Sablone ............. A61F 13/5323 156/60 |

FOREIGN PATENT DOCUMENTS

| | | |
|---|---|---|
| EP | 2905001 A1 | 8/2015 |
| EP | 3037079 A1 | 6/2016 |
| WO | 2007020562 A1 | 2/2007 |
| WO | 2014125978 A1 | 8/2014 |

OTHER PUBLICATIONS

International Search Report dated Apr. 12, 2018 from International Patent Application No. PCT/IB2018/050475.

Chinese Office Action dated Jan. 25, 2021 from counterpart CN App 201880020204.8.

* cited by examiner

APPARATUS AND METHOD FOR FORMING AN ABSORBENT PAD

This application is the National Phase of International Application PCT/IB2018/050475 filed Jan. 26, 2018 which designated the U.S.

This application claims priority to Italian Patent Application No. 102017000031317 filed Mar. 22, 2017, which application is incorporated by reference herein.

TECHNICAL FIELD

This invention relates to an apparatus and a method for forming an absorbent structure, specifically an absorbent pad or "core", as it also known in the trade, intended for use in absorbent sanitary articles such as, for example, nappies for children and adults, to which express reference is hereinafter made without losing in generality, sanitary towels and the like.

BACKGROUND ART

As is known, nappies comprise an absorbent pad or core which is normally enclosed between a permeable inner layer of non-woven fabric and an impermeable outer layer made, for example, of polyethylene.

Absorbent pads of known type comprise an absorbent core made of an absorbent material, such as, for example, granules of superabsorbent polymer material (SAP) inside a mixture of containment cellulose pulp (fluff) and absorbent material binder, sandwiched between two layers of non-woven fabric.

To improve performance in terms of absorption, comfort and distribution of absorbed liquids, pads have been developed which are provided with longitudinal channels without absorbent material between the two layers of non-woven fabric.

Document EP2905001 relates to an apparatus and a method for making an absorbent pad of this kind.

The apparatus described comprises rollers for transferring two sheets of non-woven fabric, a system for feeding the absorbent material and configured in such a way that the aforesaid channels are formed between the layers of non-woven fabric, and a system for applying adhesive used to join the two sheets.

According to the description, the rollers feed the sheets and the adhesive is spread on the sheets even at the channels; the absorbent material is spread discretely on one of the two sheets, trying to prevent it from being deposited on the channels.

Downstream of the adhesive applicators, the apparatus comprises a pressure device to optimize adhesion of the sheets to each other at the channels. More specifically, the channels are formed when the two sheets are made to adhere to each other under the combined action of the adhesive and the pressure.

One disadvantage of this system is that the glue is spread also on the zones where the channels are to be formed and the absorbent material can thus stick to the sheets in those very zones.

The pressing action applied by the pressure device can therefore damage or even perforate the pad if absorbent material is deposited between the pressure device and the mating part opposed to it.

Moreover, to obtain a satisfactory join at the channels, the pressure applied by the pressure device must be very precisely and painstakingly calibrated in order to avoid making defective nappies.

AIM OF THE INVENTION

In this context, the main purpose of this disclosure is to propose an apparatus for forming an absorbent pad to overcome the above mentioned disadvantages.

One aim of this disclosure is to propose an apparatus for forming an absorbent pad with channels which is more reliable than prior art solutions.

Another aim of this disclosure is to propose an apparatus for forming an absorbent pad with channels which allows making precise absorbent pads with effective channels.

These aims are fully achieved by an apparatus for forming an absorbent pad having the features resulting from the combination of one or more of the claims accompanying this application.

According to a first aspect of it, this disclosure relates to an apparatus for forming an absorbent pad for an absorbent sanitary article.

The pad comprises a first layer, a second layer and an absorbent material interposed between the first and the second layer and arranged according to a spreading pattern having at least one channel which is free of absorbent material.

The forming apparatus comprises a forming drum, a first feed system for feeding to the forming drum a first web, intended to form the first layer, and a second feed system for feeding to the forming drum a second web, intended to form the second layer.

The forming apparatus comprises at least one spreader for spreading the absorbent material on the forming drum and the forming drum comprises a suction system to create, for example on the first web advancing on the forming drum, a spread of absorbent material according to the absorbent material spreading pattern.

According to one aspect of this disclosure, the forming drum comprises at least one insert in the suction system to inhibit suction at the channel so that absorbent material is not retained at the channel.

The forming apparatus comprises at least one adhesive dispenser located upstream of the spreader of the absorbent material in a feed direction V of the first web to apply on the first web a layer of adhesive according to a gluing pattern and intended, for example, at least to retain the absorbent material and to contribute to joining the first and second webs.

Once joined to each other, the first web, the second web and the absorbent material form a composite web which is subsequently cut into pieces to obtain the aforesaid pads.

According to one aspect of this disclosure, the apparatus comprises a welding system for welding the first web to the second web to join the first web to the second web at least at the channel without absorbent material.

According to one aspect of this disclosure, the welding system comprises a first welding element and a second welding element acting in conjunction with each other.

The first welding element has an opposing surface for contact with the second welding element and shaped according to a welding pattern which comprises at least one welding zone at the channel.

The weld at the channel ensures a secure and reliable join.

According to one aspect of this disclosure, the welding pattern comprises a second welding zone at a first and a second longitudinal edge of the composite web so that the resulting pads have welded longitudinal edges which are more reliable than the glued edges of other solutions.

The two webs of non-woven fabric are joined by a permanent ultrasonic weld.

According to one aspect of this disclosure, the welding system is an ultrasonic welding system in which the first welding element is an anvil and the second welding element is a sonotrode acting on the anvil.

In one embodiment, the anvil is in the form of a welding roller comprising, on the outside surface of it, the opposing contact surface shaped according to the welding pattern.

According to one aspect of this disclosure, the welding roller is the forming drum which is thus provided with the opposing contact surface acted upon by the sonotrode.

The first welding element—for example a roller which acts as anvil and provided with the welding pattern—allows welding both the pad edges and the channels at the same time.

According to one aspect of this disclosure, the forming apparatus comprises a second welding system for welding the first web and the second web.

The second welding system comprises a third welding element and a fourth welding element acting in conjunction with each other.

The third welding element has a second opposing surface for contact with the fourth welding element and shaped according to a second welding pattern, different from the first welding pattern.

The second welding pattern comprises at least a second welding zone at the channel.

The first and second welding systems are used to weld absorbent pads of a first and second size, respectively, and operate alternatively; that makes the apparatus particularly versatile and capable of facilitating rapid changeovers to pads of different sizes.

The second welding system is preferably a microwave system; when there are two welding systems, the welding system that is not in operation merely constitutes a transit for the composite web.

According to one aspect of this disclosure, the gluing pattern comprises a zone which is free of adhesive at the channel.

In one embodiment, the welding pattern comprises a third welding zone transverse to the second welding zone to define a transverse end of the pad. That way, when the composite web is cut into pieces, the pads will be welded at the transverse edges as well as at the channels.

According to one aspect of this disclosure, the apparatus comprises a removal system for removing absorbent material and operating at the forming drum.

According to one aspect of this disclosure, the removal system uses a negative pressure air flow created in the spreader by the suction system which holds the absorbent material on the drum.

The removal system comprises a flow regulating system which divides the negative pressure flow when it enters the gap between the spreader and the drum.

According to one aspect of this disclosure, the regulating system comprises a valve which regulates air flow at an outlet of the gap through which the first web, with the absorbent material on it, leaves the spreader.

According to one aspect of this disclosure, the removal system for removing the absorbent material is located downstream of the absorbent material spreader in the feed direction V of the first web to remove any absorbent material that may be present on the first web at the channel.

Removing the material that may be present there allows a better quality weld to be made, thus obtaining a more reliable pad.

In one preferred embodiment, the removal system for removing the absorbent material comprises a blowing system comprising at least one centrifugal impeller whose axis of rotation is parallel to the axis of rotation of the forming drum.

The impellers preferably have an outside surface which faces the forming drum.

According to one aspect of the disclosure, the outside surface of the impellers is at least partly radially aligned with the inserts where the channels are formed.

According to one aspect of the disclosure, the impellers generate a vortex at the inserts which forces any absorbent material that may be present there towards negative pressure zones of the forming drum.

In one embodiment, the removal system for removing the absorbent material may comprise a blow nozzle which may be, for example, oriented towards the forming drum in such a way as to blow away any absorbent material that may be present at the channel, on the first web.

According to one aspect of it, this disclosure relates to a method for forming an absorbent pad for an absorbent sanitary article of the kind described above.

The method comprises a step of feeding a first web intended to form the first layer of the pad, a step of feeding a second web intended to form the second layer of the pad and a step of spreading the absorbent material on the first web according to the above mentioned absorbent material spreading pattern.

According to one aspect of this disclosure, the method preferably comprises a step of spreading an adhesive on the first web according to a gluing pattern.

Once joined to each other, the first web, the second web and the absorbent material form a composite web.

The method comprises a step of welding the first web and the second web, preferably ultrasound welding, according to a welding pattern comprising at least one welding zone at the channel.

According to one aspect of this disclosure, the method comprises a step of removing any absorbent material that may be present in the welding zone at the channel.

The step of removing the absorbent material comprises a step of blowing away any absorbent material that may be present in the welding zone at the channel.

BRIEF DESCRIPTION OF THE DRAWINGS

Further characteristics and advantages of this solution are more apparent in the non-limiting description below, with reference to a preferred but non-exclusive embodiment of a method and an apparatus for forming a pad, as illustrated in the accompanying drawings, in which.

DETAILED DESCRIPTION OF PREFERRED EMBODIMENTS OF THE INVENTION

Figure 1:
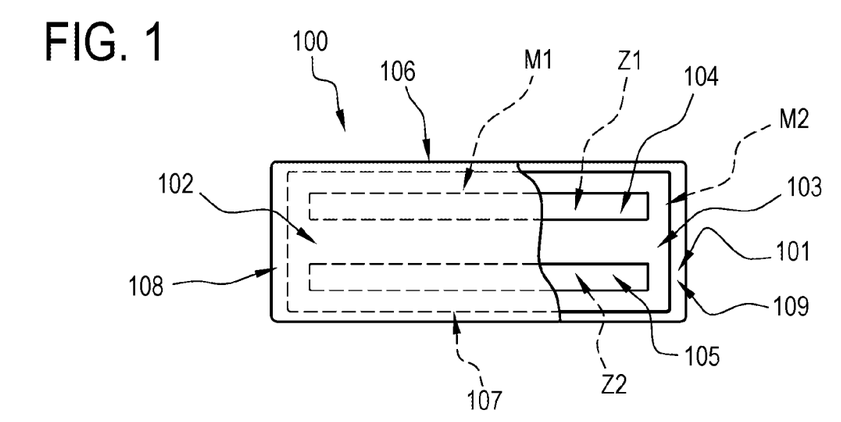
FIG. 1 is a schematic top plan view of an absorbent pad made by an apparatus according to this disclosure.

With reference to FIG. 1, the numeral 100 denotes a pad obtainable with a forming apparatus made in accordance with this disclosure.

The pad 100, intended for use in absorbent sanitary articles such as nappies for children or adults, for example, comprises a first layer 101, a second layer 102 and an absorbent material 103 interposed between the first and the second layer 101, 102 and arranged according to a spreading pattern M1.

The first and second layers 101, 102 are made, for example, of non-woven fabric and are joined to each other; the absorbent material 103 comprises, for example, cellulose fibres and superabsorbent material, also called SAP, and is fixed between the first and the second layer 101, 102.

In the example illustrated, the pattern M1, and hence the pad 100, has two zones or channels 104, 105 which are free of absorbent material and where the first and second layers 101, 102 are joined directly to each other.

In the preferred embodiment illustrated by way of example, the pad 100 has a first and a second longitudinal edge 106, 107 along which the first and second layers 101, 102 are joined directly to each other.

In the preferred embodiment illustrated by way of example, the pad 100 has a first and a second transverse edge 108, 109 along which the first and second layers 101, 102 are joined directly to each other.

Figure 2:
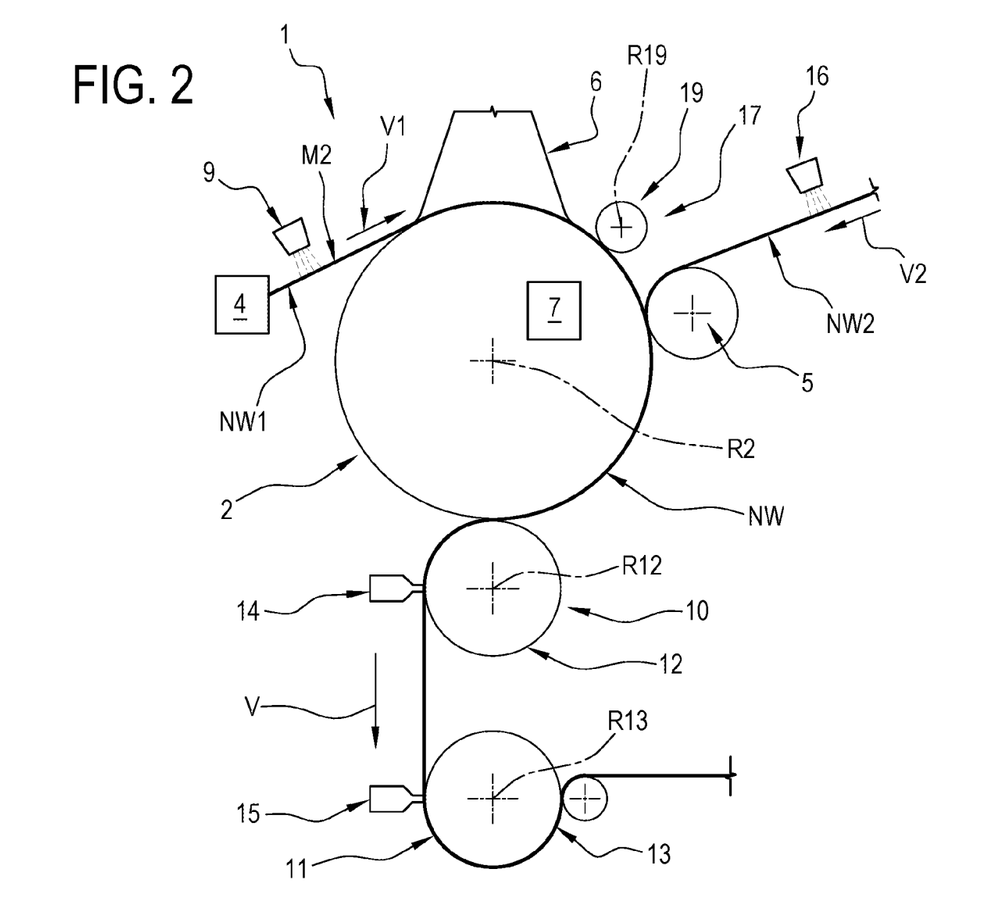
FIG. 2 is a schematic front view of a forming apparatus according to this disclosure for forming an absorbent pad.
Figure 3:
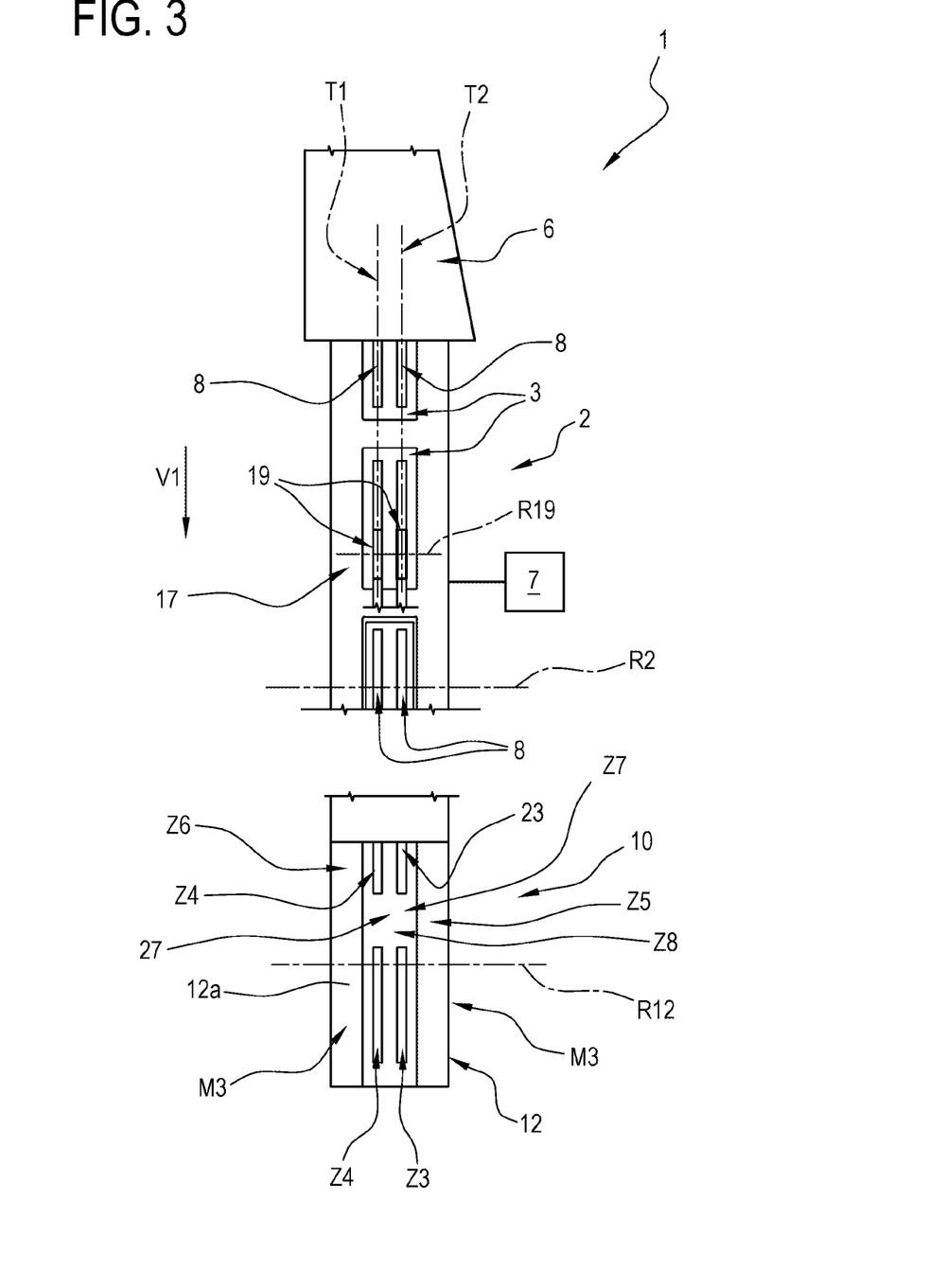
FIG. 3 illustrates the apparatus of FIG. 1 in a schematic front view, partly in blocks and with some parts cut away for greater clarity.

With reference to FIGS. 2 and 3, the numeral 1 denotes a forming apparatus for forming the pad 100 made in accordance with this disclosure.

This description of the apparatus 1 is limited to the parts necessary for understanding this invention.

The apparatus 1 comprises a drum 2 for forming the pads 100 and rotatable about an axis R2.

Along its periphery, the drum 2 comprises a plurality of seats 3, in particular for receiving the material 103, as described in more detail below.

The apparatus 1 comprises a first feed system, schematically represented as a block 4, for feeding a first web NW1 to the forming drum 2.

The web NW1 is movable in a direction V1 and is intended to form the first layer 101 of the pad 100.

The apparatus 1 comprises a second feed system, schematically represented as a block 5, for feeding a second web NW2 to the forming drum 2.

The web NW2 is movable in a direction V2 and is intended to form the second layer 102 of the pad 100.

The apparatus 1 comprises a spreader 6 for spreading the absorbent material 103 on the forming drum 2. the spreader 6 is of a substantially known type and is described only insofar as necessary for understanding this disclosure.

Figure 4:
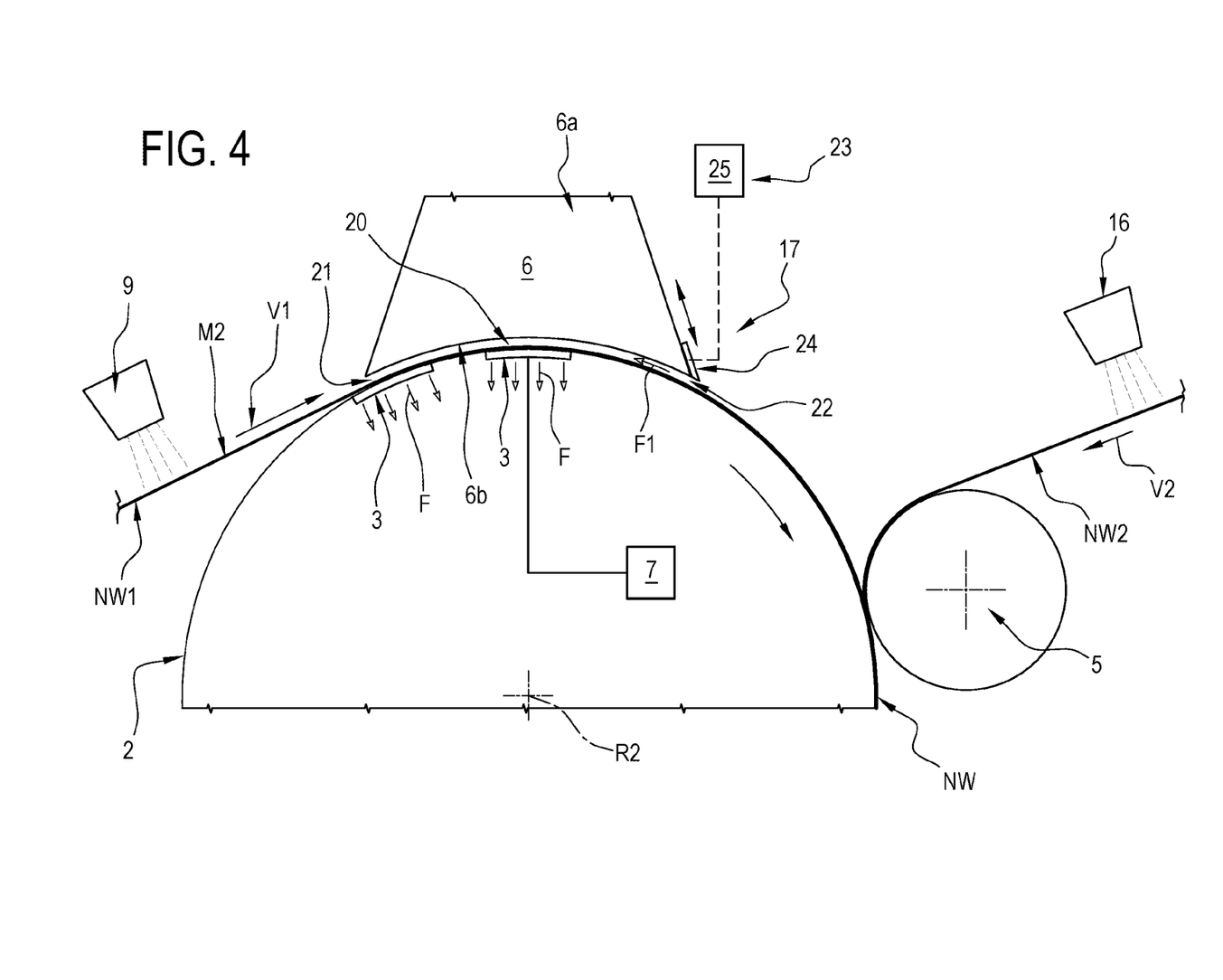
FIG. 4 is a schematic front view of a forming apparatus according to this disclosure for forming an absorbent pad.

With reference in particular to FIG. 4, the spreader 6 comprises a duct 6a having an outlet 6b, facing the drum 2, for delivering the absorbent material 103.

The duct 6a and the cylindrical outside surface of the drum 2 delimit between them a gap 20 which allows the drum 2 to rotate, clockwise in the example illustrated.

In practice, the gap is delimited by the wall of the duct 6a at the profile of the outlet 6b and the cylindrical outside surface of the drum 2.

In substantially known manner, also to prevent scattering of the absorbent material 103 and turbulence inside the duct 6a, the gap 20 is closed by suitable seals—for example, labyrinth seals—along the sides parallel to the feed direction V1 of the web NW1.

Considering the feed direction V1 of the web NW1, the apparatus 1 has an inlet 21 through which the web NW1 enters the gap 20, and an outlet 22 through which the web NW1 leaves the gap 20. The first web NW1, the second web NW2 and the absorbent material 103 together forming a composite web NW.

The forming drum 2 comprises a suction system 7, schematically represented as a block, to create on the first web NW1 fed by the drum 2, a spread of absorbent material according to the absorbent material spreading pattern M1.

The suction system 7 is in communication with the seats 3 which, in practice, are preferably suction tiles and which hold the material 103 at a predetermined position relative to the web NW1 according to the pattern M1.

A negative pressure flow F generated by the suction system 7 in substantially known manner is applied to the tiles.

The material 103 is positioned in the suction tiles which, in one embodiment, may be in the form of a continuous circular seat extending along a substantially cylindrical peripheral portion of the drum 2.

In another embodiment, of the type illustrated in the drawings, the suction tiles may be in the form of a plurality of discrete seats 3, aligned and equispaced along a substantially cylindrical peripheral portion of the drum 2.

The seats 3 may in any case be shaped to match the pad 100 and are capable of retaining by suction the absorbent material 103 transported by the drum 2.

As may be observed in particular in FIG. 3, the forming drum 2 comprises a plurality of inserts 8 in the suction system 7, positioned in particular in the seats 3, to inhibit suction at the channels 104 and 105 so that the absorbent material 103 is not retained on the web NW1 at the channels 104, 105.

The inserts 8 are, for example, solid blocks through which air cannot pass.

In the preferred embodiment illustrated, the forming apparatus comprises an adhesive dispenser 9 located upstream of the spreader 6 of the absorbent material in the feed direction V1 to apply on the first web NW1 a layer of adhesive according to a pattern M2 for gluing the absorbent material 103.

In a preferred embodiment, the gluing pattern M2 corresponds to the absorbent material pattern M1, that is to say, the adhesive is applied on the web NW1 in the zones where the absorbent material 103 is to be deposited.

More specifically, the gluing pattern M2 comprises zones Z1, Z2 which are free of adhesive, corresponding to the channels 104, 105.

In alternative embodiments not illustrated, no adhesive is applied before the absorbent material is spread.

A preferred embodiment of the apparatus 1 comprises a welding system 10 to join the first and second webs NW1, NW2 according to a welding pattern M3.

In the preferred embodiment illustrated by way of example, the apparatus 1 comprises a welding system 10 to join the first and second webs NW1 and NW2 according to a welding pattern M3 and a welding system 11 to join the first and second webs NW1 and NW2 according to a welding pattern M4.

The systems 10 and 11 are preferably used to weld pads 100 of different sizes and operate alternatively, that is to say, when the system 10 is operating, the web NW passes through the system 11 in transit only, and vice versa.

Preferably, the apparatus 1 comprises an ultrasonic welding system 10, 11.

The systems 10 and 11 each comprise a first welding element 12, 13 which, in the example illustrated, is defined by a welding roller rotatable about a respective axis of rotation R12, R13.

The systems 10 and 11 each comprise a second welding element 14, 15 which, in the example illustrated, is defined by a sonotrode.

The rollers 12 and 13 each define, for the respective sonotrodes, a welding anvil.

Each first welding element 12, 13 has an opposing surface for contact with the respective second welding element and shaped according to the respective welding pattern M3, M4.

The welding roller 12 with the respective welding pattern M3 is illustrated by way of an example in FIG. 3; the pattern M4 is conceptually identical to the pattern M3 and is therefore not described further.

The welding roller 12 has an opposing surface 12a for contact with the sonotrode 14 and shaped according to the respective welding pattern M3.

The pattern M3 comprises a welding zone Z3, Z4 corresponding to the channels 104, 105.

In practice, the surface 12a is shaped to define an anvil for the sonotrode 14 in the zones Z3, Z4 corresponding to the channels 104 and 105.

In a preferred embodiment of the apparatus 1, the pattern M3 comprises a welding zone Z5, Z6 at the longitudinal edges 106, 107 of the pad 100.

In practice, the surface 12a is shaped to define an anvil for the sonotrode 14 in the zones Z5, Z6 corresponding to the longitudinal edges 106 and 107 of the pad 100.

In an embodiment not illustrated, the pattern M3 comprises a welding zone Z7, Z8 at the transverse edges 108, 109 of the pad 100.

In practice, the surface 12a is shaped to define an anvil for the sonotrode 14 in the zones Z7, Z8 corresponding to the transverse edges 108 and 109 of the pad 100.

In an embodiment not illustrated, the welding roller, that is, the first welding element of the welding system 10, is the forming roller 2.

In such a case, the forming roller 2, which in the case of ultrasonic welding, constitutes the anvil of the system, comprises a respective opposing surface for contact with the sonotrode and shaped, for example, according to the welding pattern M3.

In the roller 2, the aforementioned inserts 8 may, for example, constitute the opposing surfaces for contact with the sonotrode.

In the embodiment illustrated by way of example, the apparatus 1 comprises a second adhesive dispenser 16 for applying a layer of adhesive on the web NW2 in order to optimize adhesion of the web NW2 to the first web NW1.

According to one aspect of this disclosure, the apparatus 1 comprises a removal system 17 for removing any absorbent material that may be present on the first web NW1 at the inserts 8, that is, in the zones of the web which will constitute the channels 104, 105.

In an embodiment illustrated by way of example in FIGS. 2 and 3, the system 17 is operates at the forming drum 2 and is mounted downstream of the spreader 6 of the absorbent material 103 in the feed direction V1 of the first web NW1.

In the embodiment illustrated by way of example, the removal system 17 for removing the absorbent material comprises a blowing system 18 which can blow away from the web NW1 any absorbent material 103 that may be present at the inserts 8, that is, at the channels 104 and 105. The material 103 may be blown onto the suction zones, where it is retained by the system 7.

According to one aspect of the disclosure, the blowing system 18 comprises at least one centrifugal impeller 19 whose axis of rotation R19 is parallel to the axis of rotation R2 of the drum 2; in the example illustrated, the system comprises two coaxial impellers 19, each disposed at a respective channel 104, 104, downstream of the device 6.

As illustrated schematically in FIG. 2, the impellers 19 have an outside surface which faces the drum 2.

According to one aspect of the disclosure, the impellers 19 generate a vortex at the inserts 8 which forces any absorbent material 103 that may be present there towards negative pressure zones of the drum 2.

The vortex preferably has a tangential component substantially tangent to the cylindrical outside surface of the drum 2.

In alternative embodiments, the blowing system comprises nozzles which blow air at the inserts 8 and which are preferably oriented towards the forming drum 2.

Preferably, the impellers 19, or the blowing nozzles, are disposed along the trajectories T1, T2 followed by the inserts 8 as the drum 2 rotates about the axis R2.

The impellers 19, or the blowing nozzles, are also optimized to prevent the blown air from modifying the pattern of the absorbent material 103 spread near the channels.

In alternative embodiments not illustrated, the removal system 17 for removing the absorbent material may, for example, comprise brushes acting on the web NW1 and/or a suction system for extracting the absorbent material and/or a scraper to ensure that the web NW1 remains clean at the channels 104, 105 where it will be welded.

During operation of the apparatus 1, the system 7 generates a negative pressure within the duct 6a which creates a negative pressure air flow F1 from the outside to the inside of the spreader 6.

The flow F1 enters the duct 6a predominantly through the gap 20.

Since the sides of the gap 20 are closed, the flow F1 enters predominantly through the outlet 22.

In an embodiment illustrated by way of example in FIG. 4, the removal system 17 for removing the absorbent material 103 comprises a system 23 for regulating the negative pressure air flow F1 within the spreader 6 so that the flow F1, when suitably regulated, removes any absorbent material 103 that may be present on the web NW1 at the inserts 8.

In this embodiment, the removal system 17 for removing the material comprises the suction system 7 and the regulating system 23 which is configured to regulate the air flow F1 at the outlet 22.

Preferably, the regulating system 23 is at least partly disposed outside the duct 6a so as to reduce the effect on the spread of absorbent material 103.

In an embodiment illustrated by way of example, the system 23 comprises a valve 24 for at least partly closing the gap 20.

As illustrated, the valve 24 operates at the outlet 22 and is movable between a first operating configuration where the outlet 22 is open and a second operating configuration where the outlet 22 is at least partly closed.

In alternative embodiments not illustrated, the valve 24 may be located at the inlet 21 or there may be two valves, one at the inlet and one at the outlet of the gap.

There might also be an inlet for the air sucked into the sides of the gap 20 in such a way that the suitably controlled flow F1 can remove the material from the web NW1 at the inserts 8.

In the embodiment illustrated, the system 23 comprises an actuator, schematically represented as a block 25, to drive the valve 24 and adjust valve opening as a function of the expected flow F1.

The valve 24 may also be set in such a way as to never completely prevent air from entering the gap 20, irrespective of the need to leave the drum 2 free to rotate.

Preferably, at least the valve 24 is disposed outside the duct 6a, as illustrated schematically by way of example.

According to one aspect of it, this disclosure has for an object a method for forming the absorbent pads 100 as described in the foregoing and illustrated in FIG. 1.

With reference, for example, to FIGS. 2 and 3, the method for forming an absorbent pad 100 comprises a step of feeding to the forming drum 2 the first web NW1, intended to form the first layer 101, a step of feeding to the forming drum 2 the second web NW2, intended to form the second layer 102, a step of spreading the absorbent material 103 on the first web NW1 according to the spreading pattern M1 and a step of spreading adhesive on the first web NW1 according to the gluing pattern M2.

According to one aspect of this disclosure, the method comprises a step of welding the first and second webs NW1, NW2, for example using ultrasound, according to the welding pattern M3 or M4, which comprises the welding zones Z3, Z4 at the channels 104, 105.

According to one aspect of this disclosure, the method comprises a step of removing any absorbent material 103 that may be present on the web NW1 in the welding zones Z3, Z4 where the channels 104, 105 will be defined.

In a preferred embodiment, illustrated by way of example, the step of removing the absorbent material 103 comprises a step of blowing away from the web NW1 any absorbent material 103 that may be present in the welding zones Z3, Z4 at the channels 104, 105 in order to clean the web so it is ready for subsequent welding.

Since the channels 104, 105 are not continuous along the composite web NW, and hence the zones 104, 105 free of absorbent material on the web NW1 are not continuous, the step of blowing is intermittent.

In one embodiment, the step of removing the absorbent material 103 comprises a step of suitably regulating the airflow drawn into the spreader 6 by the suction system 7.

In that case, the method preferably comprises a step of adjusting the opening or cross section size of the outlet 22 by means of a suitable regulating system in such a way as to modify one or more properties of the air flow F1 entering the gap 20.

The invention claimed is:

1. An apparatus for forming an absorbent pad for an absorbent sanitary article, the pad comprising a first layer, a second layer and an absorbent material interposed between the first layer and the second layer and arranged according to an absorbent material spreading pattern including a channel which is free of absorbent material, the apparatus comprising:
   a forming drum including a permeable surface,
   a first feeder for feeding to the forming drum a first web, configured to form the first layer,
   a second feeder for feeding to the forming drum a second web, configured to form the second layer,
   a spreader including a duct for spreading the absorbent material on the forming drum and positioned with respect to the forming drum to create a gap between the spreader and the forming drum,
   wherein the forming drum comprises a suction system, the suction system including the permeable surface to draw an air flow into the spreader through the gap to create on the first web disposed on the forming drum a spread of absorbent material according to the absorbent material spreading pattern, the forming drum further including an insert positioned to inhibit suction at the channel so that the absorbent material is not retained at the channel,
   wherein the first web, the second web and the absorbent material together form a composite web,
   a joining system including a welder for joining the first and second webs and located downstream of the second feeder, and
   a removal system for removing the absorbent material to remove any absorbent material that may be present on the first web at the channel,
   wherein the removal system for removing the absorbent material comprises the suction system and a regulating system for regulating a negative pressure of the air flow into the spreader through the gap.

2. The apparatus according to claim 1, wherein the gap has an inlet and an outlet for the first web, the regulating system being configured to regulate the air flow at the outlet.

3. The apparatus according to claim 1, wherein the regulating system comprises a valve for at least partly adjusting an extent of the gap.

4. The apparatus according to claim 3, wherein the gap has an inlet and an outlet for the first web, and the valve is positioned at the outlet.

5. The apparatus according to claim 3, further comprising an actuator for driving the valve.

6. The apparatus according to claim 1, wherein the duct has an outlet, facing the forming drum, for delivering the absorbent material and the regulating system is at least partly disposed outside the duct.

7. The apparatus according to claim 1, wherein the removal system for removing the absorbent material further comprises, downstream of the spreader in a feed direction of the first web and comprises, a blowing system comprising at least one centrifugal impeller, each of the at least one centrifugal impeller having an axis of rotation parallel to an axis of rotation of the forming drum.

8. The apparatus according to claim 7, wherein an outside surface of each of the at least one centrifugal impeller faces the forming drum.

9. The apparatus according to claim 7, wherein each of the at least one centrifugal impeller is at least partly aligned, in a radial direction, with the insert.

10. The apparatus according to claim 1, further comprising at least one adhesive dispenser located upstream of the spreader in a feed direction of the first web to apply on the first web a layer of adhesive according to a gluing pattern comprising a zone which is free of adhesive at the channel.

11. An apparatus for forming an absorbent pad for an absorbent sanitary article, the pad comprising a first layer, a second layer and an absorbent material interposed between the first layer and the second layer and arranged according to an absorbent material spreading pattern including a channel which is free of absorbent material, the apparatus comprising:
   a forming drum including a permeable surface,
   a first feeder for feeding to the forming drum a first web, configured to form the first layer,
   a second feeder for feeding to the forming drum a second web, configured to form the second layer,
   a spreader including a duct for spreading the absorbent material on the forming drum and positioned with respect to the forming drum to create a gap between the spreader and the forming drum,
   wherein the forming drum comprises a suction system, the suction system including the permeable surface to draw an air flow into the spreader through the gap to create on the first web disposed on the forming drum a spread of absorbent material according to the absorbent material spreading pattern, the forming drum further including an insert positioned to inhibit suction at the channel so that the absorbent material is not retained at the channel, wherein the first web, the second web and the absorbent material together form a composite web, a joining system including a welder for joining the first and second webs and located downstream of the second feeder, and a removal system for removing the absorbent material to remove any absorbent material that may be present on the first web at the channel, wherein the removal system for removing the absorbent material is located downstream of the spreader in a feed direction of the first web and comprises a blowing system comprising at least one centrifugal impeller, each of the at least one centrifugal impeller having an axis of rotation parallel to an axis of rotation of the forming drum.

12. The apparatus according to claim 11, wherein an outside surface of each of the at least one centrifugal impeller faces the forming drum.

13. The apparatus according to claim 11, wherein each of the at least one centrifugal impeller is at least partly aligned, in a radial direction, with the insert.

14. A method for forming an absorbent pad for an absorbent sanitary article, the pad comprising a first layer, a second layer and an absorbent material interposed between the first layer and the second layer and arranged according to a spreading pattern having at least one channel which is free of absorbent material, the method comprising:

providing an apparatus, comprising:
a forming drum including a permeable surface,
a first feeder for feeding to the forming drum a first web, configured to form the first layer,
a second feeder for feeding to the forming drum a second web, configured to form the second layer,
a spreader including a duct for spreading the absorbent material on the forming drum and positioned with respect to the forming drum to create a gap between the spreader and the forming drum,
wherein the forming drum comprises a suction system, the suction system including the permeable surface to draw an air flow into the spreader through the gap to create on the first web disposed on the forming drum a spread of absorbent material according to the absorbent material spreading pattern, the forming drum further including at least one insert positioned to inhibit suction at the at least one channel, respectively, so that the absorbent material is not retained at the at least one channel, wherein the first web, the second web and the absorbent material together form a composite web, a joining system including a welder for joining the first and second webs and located downstream of the second feeder, and a removal system for removing the absorbent material to remove any absorbent material that may be present on the first web at the at least one channel, wherein the removal system for removing the absorbent material comprises the suction system and a regulating system for regulating a negative pressure of the air flow into the spreader through the gap, feeding the first web, intended to form the first layer, with the first feeder to the forming drum, feeding the second web, intended to form the second layer, with the second feeder to the forming drum, spreading the absorbent material on the first web according to the spreading pattern using the spreader, joining the first and second webs together with the joining system such that the absorbent material is between the first and second webs, wherein the first web, the second web and the absorbent material together form a composite web, and removing any absorbent material that may be present in a welding zone of the first web at the at least one channel using the removal system.

15. The method according to claim 14, wherein removing any absorbent material comprises blowing away any absorbent material that may be present in the welding zone of the first web at the at least one channel by generating a vortex having a tangential component tangent to the first web in the welding zone at the at least one channel.

16. The method according to claim 15, wherein the blowing is intermittent.

17. The method according to claim 14, further comprising spreading an adhesive on the first web according to a gluing pattern comprising a zone which is free of adhesive at the at least one channel.

18. The method according to claim 14, further comprising holding by suction the absorbent material spread on the first web, wherein removing any absorbent material comprises regulating the negative air flow entering the gap with the regulating system.

19. The method according to claim 18, wherein the negative air flow is generated by the step of holding by suction the absorbent material spread on the first web.

20. The method according to claim 18, wherein regulating the negative air flow entering the gap is accomplished by varying a cross-sectional size of an outlet of the gap.

* * * * *